United States Patent [19]

Chen

[11] Patent Number: 5,260,068
[45] Date of Patent: Nov. 9, 1993

[54] MULTIPARTICULATE PULSATILE DRUG DELIVERY SYSTEM

[75] Inventor: Chih-Ming Chen, Cooper City, Fla.

[73] Assignee: Anda SR Pharmaceuticals Inc., Hollywood, Fla.

[21] Appl. No.: 878,416

[22] Filed: May 4, 1992

[51] Int. Cl.⁵ .............................................. A61K 9/48
[52] U.S. Cl. ...................................... 424/451; 424/482; 424/489; 424/490; 424/497
[58] Field of Search ................ 424/490, 489, 497, 482

[56] References Cited

U.S. PATENT DOCUMENTS

| | | | |
|---|---|---|---|
| 4,851,229 | 7/1989 | Magruder | 424/457 |
| 4,894,240 | 1/1990 | Geoghegan et al. | 424/489 |
| 4,917,899 | 4/1990 | Geoghegan et al. | 424/497 |
| 5,000,962 | 3/1991 | Sangekar et al. | 424/482 |
| 5,011,692 | 4/1991 | Fujioka | 424/426 |
| 5,017,381 | 5/1991 | Maruyama | 424/472 |
| 5,112,621 | 3/1992 | Stevens et al. | 424/497 |

Primary Examiner—Thurman K. Page
Assistant Examiner—William Benston, Jr.
Attorney, Agent, or Firm—Alvin S. Blum

[57] ABSTRACT

A unit dosage form of capsule, tablet or the like is composed of a large number of pellets made up of two or more populations of pellets or particles. Each pellet contains a core containing the therapeutic drug and a water soluble osmotic agent. A water-permeable, water-insoluble polymer film encloses each core. Incorporated into the polymer film is a hydrophobic, water insoluble agent which alters the permeability of the polymer film. The film coating of each population of pellets differs from the coating of every other population of pellets in the dosage form in the rate at which water passes through to the core and the rate at which drug diffuses out of the core. The osmotic agent dissolves in the water, causing the pellet to swell and regulating the rate of diffusion of drug into the environment of use. As each population of pellets releases its drug into the environment sequentially, the effect is to provide a series of pulsatile administrations of the drug from a single dosage form.

20 Claims, 1 Drawing Sheet

MULTIPARTICULATE PULSATILE DRUG DELIVERY SYSTEM

BACKGROUND OF THE INVENTION

This invention relates to a controlled absorption pharmaceutical preparation and more particularly to a unit dosage form of an assemblage of a plurality of different populations of particles that, upon administration, release therapeutic agents in a sequential, pulsatile fashion.

Many therapeutic agents are most effective when present at a uniform concentration in the blood. They may be ineffective at a lower level and toxic at a higher level, causing, for example, cardiac, kidney or hearing injury. A reasonably constant, effective and safe blood level may be achieved by intravenous infusion of a uniform solution of the drug directly into the blood. This is not practical in most situations such as veterinary medicine, long term medication, and ambulatory health care outside of the hospital, where oral dosage formulations may achieve a therapeutic effect. A single daily dose will generally cause the blood level to rise to a peak and then fall of as the drug is first absorbed into the blood and then excreted or metabolized. To achieve a more uniform blood level, the drug may be administered in divided doses over timed intervals throughout the day, to produce a pulsatile blood concentration curve with time. In some situations this may be more effective than a uniform blood level. It is inconvenient to take many dosage units throughout the day. It may also be more prone to error from missed doses and double doses.

U.S. Pat. No. 4,851,229 issued Jul. 25, 1989 to Magruder et al discusses relative merits of steady state versus pulsatile drug delivery regimens and discloses a unit dosage form of complex structure for pulsatile delivery of drug employing an osmotic pump mechanism and a semi permeable shell with a tiny hole in the shell through which the drug is ejected.

U.S. Pat. No. 5,011,692 issued Apr. 30, 1991 to Fujioka et al discloses a preparation with multiple layers for a pulsatile release effect.

U.S. Pat. No. 5,017,381 issued May 21, 1991 to Maruyama et al discloses a plurality of cup shaped elements within a housing to provide a pulsatile delivery system.

These systems require special manufacturing procedures and equipment for the special structures that are costly and may be less reliable than conventional pharmaceutical manufacturing procedures. They may not be as readily controlled for particular time intervals. They are not readily adapted to a large number of pulses in a single dosage form as may be most desirable in a rapidly absorbed and excreted drug having a short useful half-life in the blood.

SUMMARY OF THE INVENTION

It is accordingly an object of the invention to provide unit dosage forms for drugs or therapeutic agents that will release the drug into the environment of use in a series of sequential, pulsatile releasing events that employs conventional pharmaceutical equipment and products for optimum economy and reliability. It is another object to provide dosage units readily adaptible to a variety of timing intervals, different therapeutic agents and combinations of agents. It is yet another object to provide a system that can yield a large number of pulses within a single unit dosage form at no significant increase in cost over only one or two pulses. It is yet another object to provide means for protecting the drug from adverse environmental conditions prior to delivery into the environment of use.

The multiparticulate pulsatile drug system of the invention comprises at least two different populations of polymer film coated pellets containing drug and osmotic agent. Each pellet has a coating of water-permeable, water-insoluble, film-forming polymer material in combination with substantial amounts of a hydrophobic agent to control the rate of penetration of water into the core and the lag time before release of drug into the environment.

The coating on the pellets of each population being sufficiently different from the coating on the pellets of every other population in the unit dose to provide pulses of drug separate from one another by a substantial time interval so that a single dose administration results in a sequence of pulses of drug being released into the blood throughout the day. The rate of release may be controlled by varying the thickness of the coat, the proportion of hydrophobic agent in the coating, and the proportion of osmotic agent in the pellet.

These and other objects, advantages and features of the invention will become more apparent when the detailed description is considered in conjunction with the drawings, in which:

DETAILED DESCRIPTION OF PREFERRED EMBODIMENTS

Figure 1:
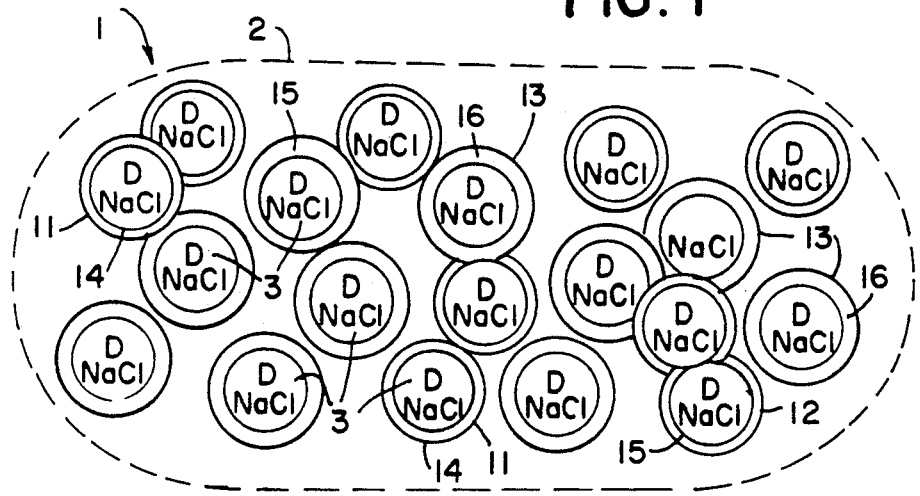
FIG. 1 shows a diagrammatic representation of a unit dosage form of the invention.
Figure 2:
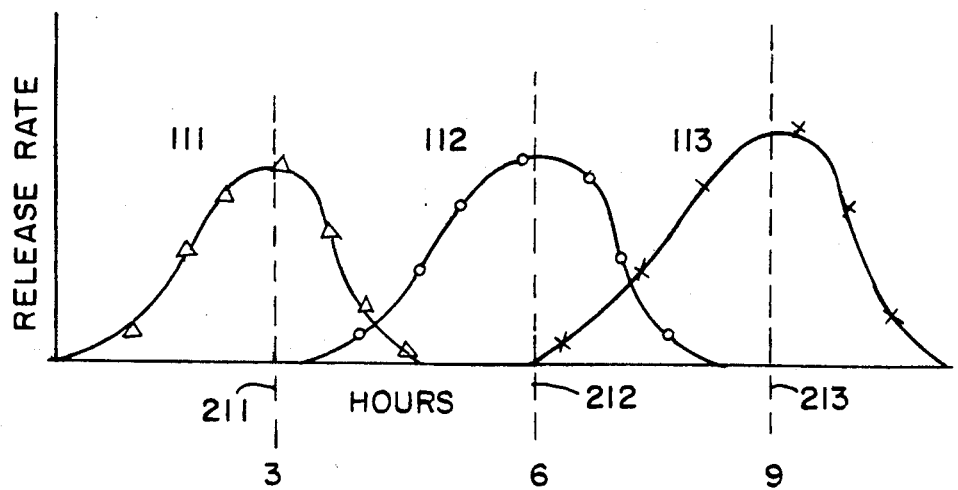
FIG. 2 is a composite graph depicting delivery of drug into an aqueous environment from three populations of pellets.

Referring now first to FIGS. 1 and 2, the unit dose 1 comprises a gelatin capsule 2 containing three populations of pellets 11, 12 and 13. Each pellet contains a core 3. The core contains a drug D and a water soluble modulating agent, in this case sodium chloride (NaCl). These are held in place by a binding agent such as polyvinylpyrrolidone. Completely enclosing each core 3 is a protective film coating made from a water insoluble, water permeable film-forming polymer material. The thickness of coating is uniform within a population and the coating thickness determines the lag time before the drug D is released into the environment of use. The first population of pellets 11 have a thin coating 14, the second population of pellets 12 have a thicker coating 15, and the third population of pellets 13 have the thickest coating 16. When the dosage form is exposed to the appropriate environment of use, such as the fluid in the gut, the vagina, or the anus, the capsule 2 is dissolved, or loses its integrity, and the pellets are directly exposed to the fluid. Water diffuses slowly through the coating to reach the core 3 and wet the drug D and the modulating or osmotic agent NaCl. The osmotic agent competes with the drug for the water. As the osmotic agent goes into solution, the osmotic pressure in the core increases, more water is drawn in and the pellets swell. This is clearly visible in vitro, where they may double in size. This thins the membrane. The dissolved drug diffuses through the thinner membrane more rapidly. FIG. 2 shows graphically how the pellets of the three populations release their drug into an aqueous environment. Superimposed upon a single set of coordinates are the release profiles for each of the three populations of pellets, the graph 111 representing the concentration of the drug in solution versus time for the pellets 11, graph 112 for the pellets 12 and graph 113 for the pellets 13, all done in vitro in water at 37° C. It is evident that the mean release time, the time when half of the drug in the pellets has been released, of each population of pellets, times 211, 212, 213 are separated from one another by a time greater than one hour to ensure effective pulsatile administration of drug.

The pH of various portions of the gut is considerably variable and the transit time of solids through the gut is also variable both between individuals and within the same individual under different circumstances. To ensure that these variables do not defeat the objective of preset release time intervals, the coating may be made of material that is substantially pH independent in its properties over the pH range encountered in the environment of use. The coating is comprised of water-permeable, water-insoluble, film-forming polymer material such as cellulose ether derivatives, acrylic resins, copolymers of acrylic acid and methacrylic acid esters with quaternary ammonium groups, and copolymers of acrylic acid and methacrylic acid esters. Combined with the polymer material is a hydrophobic agent such as the fatty acids, waxes, and the salts of the fatty acids such as magnesium stearate and calcium stearate. The pharmaceutical grades may not be pure stearates but may contain small amounts of other fatty acid salts. The hydrophobic agents are added to reduce the permeability of the coating to water and are added in amounts of from 25% to more than 50% of the amount of polymer material. It is common practice to add small amounts of stearates to coatings to reduce tackiness, but not such very large amounts to reduce permeability. Plasticizers may also be added to the coating material to reduce brittleness.

Figure 3:
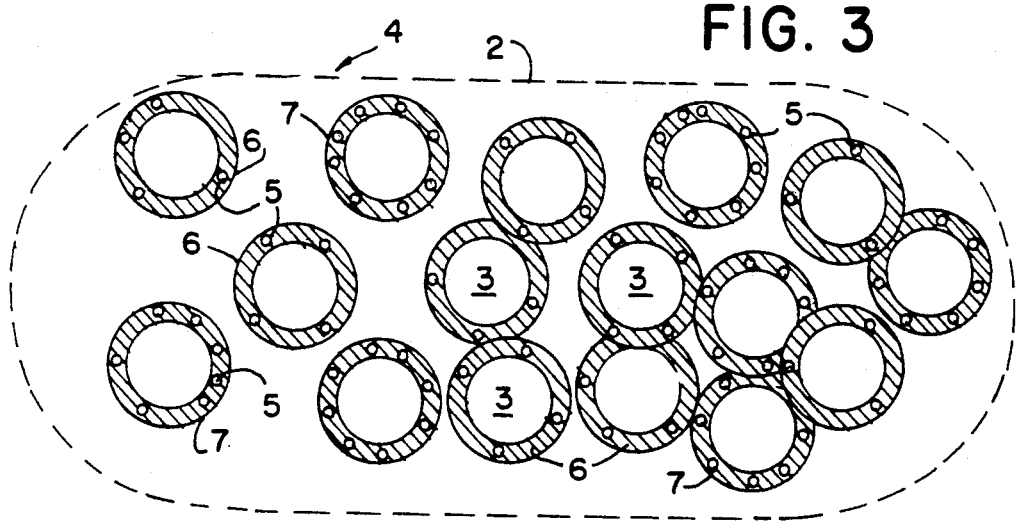
FIG. 3 shows a diagrammatic representation of another unit dosage form of the invention.

Referring now to FIG. 3, another embodiment of the invention 4 is shown in which there are two populations of pellets within a capsule 2. The cores 3 may be formed as in FIG. 1. The coatings are all of substantially the same thickness, but their permeability to water differs as a result of having different proportions of the hydrophobic agent, magnesium stearate represented by the small circles 5. The rapid release pellets 6 have magnesium stearate in amount thirty percent of the polymer material and the slow release pellets 7 have fifty percent of magnesium stearate, or processing aids. Other agents, well known in the pharmaceutical art may be used such as various plasticizers, binding material agents and the like. The pellets may be mixed with a carrier medium or binder which medium loses its integrity when exposed to the body cavity environment of use so that the pellets may be formed into a unit dose form of tablets, suppositories and the like, which will disintegrate in the environment of use to release the pellets. The unit dose form may be a pouch from which the assemblage of populations of pellets are emptied into food or other dosage forms well known in the art.

The following examples describe typical formulations of multiparticulate, pulsatile unit dosage forms and methods of manufacture thereof:

EXAMPLE I 80 grams of sodium chloride and 24 grams of polyvinylpyrrolidone are dissolved in 1.2 kilograms of water and 400 grams of pulverized diltiazem hydrochloride are suspended therein.

In a fluidized bed coater, 400 grams of starch/sugar seeds (30/50 mesh) are suspended in warm air and spray coated with the diltiazem suspension until the seeds are uniformly coated with the desired drug potency.

Magnesium stearate in isopropyl alcohol is mixed with Eudragit NE30D with is a trademarked aqueous dispersion of a neutral copolymer based on ethyl acrylate and methyl methacrylate having 30% dry substance, obtained from Rohm Pharma of Weiterstadt, Germany, in a proportion of two to 1 of dried polymer to magnesium stearate. A sufficient amount of the polymer suspension is sprayed onto the active cores to provide a particular film coating thickness to achieve a particular lag time and rate of release for a population of pellets. The final coated pellets are dried at 50° C. for 2 hours to assure complete removal of moisture to stabilize the core contents.

The procedure is repeated with at least one more batch using a different coating thickness to have a different lag time and rate of release. In this example, two populations are prepared, one with a 10% weight gain and one with a 30% weight gain of coating. Unit doses are prepared by mixing the two populations together in predetermined proportions and filling capsules with the mixture.

EXAMPLE II

The active cores are prepared as in example I. Magnesium stearate and triacetin plasticizer are mixed with Eudragit RS 30D suspension in a dry weight ratio of 1:0.6:2, where Eudragit RS 30D is a trademarked aqueous dispersion of a copolymer based on acrylic and methacrylic acid esters with a low content of quaternary ammonium groups.

The polymer suspension is coated on the cores as for example I, preparing a plurality of populations, each having a particular coating thickness to provide a particular lag time and rate of release of drug in an aqueous environment of use.

The different population of pellets are mixed and the mixture used to fill capsules as described for example I.

Fluidized bed coaters are well known in the art and have been found useful in this process but other coating apparatus and methods well known in the art may be used with the invention as well.

The terms "therapeutic agent" and "drug" as used herein includes, without limitation, antibiotics, tranquilizers, agents acting on the heart, liver, kidney, central nervous system and muscles, contraceptives, hormonal agents, antineoplastic agents useful in humans or animals and may include combinations of drugs.

The terms "carrier medium" and "unit dosage form" include, without limitation, discrete aggregates of populations of pellets contained in capsules, well known in the pharmaceutical art as a carrier medium whose integrity is not maintained in the environment of use, i.e. the capsule dissolves in the body fluid, or compressed into tablets or suppositories with binding agent as a carrier medium whose integrity is not maintained in the environment of use. The dosage form may be arranged to dissolve promptly in any aqueous medium or to resist dissolution in certain environments such as enteric coated tablets which will not release pellets until they have passed the acid stomach, whose pH may be as low as 1, and reached the alkaline intestine whose pH may be 7.5.

In an alternative embodiment of the invention, a first population of coated, drug containing pellets with delayed release properties as described above is combined with a second population of pellets that do not have a delayed release coating to provide a two pulse dosage unit, the first pulse appearing promptly when the pellets of the second population are exposed to the environment and the second pulse being delayed by the special coating on the first population of pellets. Optionally all of the therapeutic agent in the unit dosage form may be in a single population to provide a single pulse, delayed by the release-controlling coating.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention within the scope of the appended claims.

I claim:

1. A unit dosage form for administering a therapeutic agent into an aqueous fluid-containing environment in a plurality of sequential, pulsatile releasing events, said unit dosage form comprising:
   a) a capsule which does not maintain its integrity in the environment of use;
   b) a plurality of populations of pellets held together by said capsule, each population of pellets arranged to release into said environment the therapeutic agent at a different time after contact with said environment;
   c) each pellet comprising: 1) a core including said therapeutic agent, and a modulating agent which is a different agent than the therapeutic agent, said modulating agent being soluble in water and providing an osmotic effect when dissolved; and 2) a coating enclosing said core, said coating comprised of at least one water-permeable, film-forming, water-insoluble polymer material and a hydrophobic agent, said hydrophobic agent is selected from the group consisting of fatty acids, waxes and salts of fatty acids, said hydrophobic agent present in an amount of at least twenty-five percent of said water insoluble polymer material, all of a population of pellets being provided with a substantially uniform coating that causes water to enter said core and therapeutic agent to diffuse through the coating and into said environment at a particular time after exposure to said environment; and
   d) each population of pellets being provided with a coating which causes said therapeutic agent to be released at a different time into the environment of use than other populations of pellets to thereby provide a plurality of sequential therapeutic releasing events when said populations are all exposed to said environment at the same time, with each population providing a different time of release of said therapeutic agent, and in which each population of pellets has a mean release time in said environment of use that is separated from the mean release time of every other population of pellets by at least one hour.

2. The unit dosage form according to claim 1, in which the pellets of each population differs from the other populations in the thickness of the coating.

3. The unit dosage form according to claim 2, in which said film-forming, water insoluble polymer material is at least one member of the group consisting of copolymers of acrylic and methacrylic acid esters, copolymers of acrylic and methacrylic acid esters with quaternary ammonium groups, cellulose ether derivatives, and acrylic resins.

4. The dosage form according to claim 2, in which said therapeutic agent is a pharmaceutically acceptable form of diltiazem, said core includes at least one processing aid, and said film-forming polymer material comprises a copolymer of acrylic and methacrylic acid esters with less than six percent quaternary ammonium groups in combination with at least one plasticizing agent and said hydrophobic agent being a stearate salt present in an amount of at least forty percent of said polymer material.

5. The dosage form according to claim 2, in which said therapeutic agent is a pharmaceutically acceptable form of diltiazem, said core includes at least one processing aid, and said polymer material includes a copolymer of acrylic and methacrylic acid esters and said hydrophobic agent being stearate salt present in an amount of at least forty percent of said polymer material.

6. The dosage form according to claim 2, in which there are at least two populations of pellets.

7. The dosage form according to claim 2, in which there are at least three populations of pellets.

8. The unit dosage form according to claim 1, in which the pellets of each population differ from the other populations in the proportion of said hydrophic agent to said polymer material in the coating enclosing said pellets.

9. The unit dosage form according to claim 8, in which said polymer material is at least one member of the group consisting of copolymers of acrylic and methacrylic acid esters, copolymers of acrylic and methacrylic acid esters with quaternary ammonium groups, cellulose ether derivatives, and acrylic resins.

10. The unit form according to claim 8, in which said therapeutic agent is a pharmaceutically acceptable form of diltiazem, said core includes at least one processing aid, and said polymer material comprises a copolymer of acrylic and methacrylic acid esters with less than six percent quaternary ammonium groups in combination with at least one plasticizing agent and said hydrophobic agent is a stearate salt.

11. The dosage form according to claim 8, in which said therapeutic agent is a pharmaceutically acceptable form of diltiazem, said core includes at least one processing aid, and said polymer material includes a copolymer of acrylic and methacrylic acid esters and said hydrophobic agent is a stearate salt.

12. The dosage form according to claim 8, in which there are at least three populations of pellets.

13. The dosage form according to claim 8, in which there are at least two populations of pellets.

14. The dosage form according to claim 1, in which the amount of modulating agent within the cores of the pellets in any one population of pellets differs from the amount of modulating agent in any other population of pellets to contribute to the control of the time of release.

15. The dosage form according to claim 1, in which said capsule is a gelatin capsule.

16. The dosage form according to claim 1, in which said polymer material is pH independent over the pH range encountered in the environment of use.

17. A method for preparing unit dosage forms for administering a therapeutic agent into an aqueous environment of use in a plurality of sequential, pulsatile releasing events, the method comprising the steps of:
   a) forming a plurality of cores as defined in claim 1;
   b) coating a first population of said cores uniformly with a coating as defined in claim 1, thereby forming a population of film coated pellets, said pellets having a defined permeability to water and said therapeutic agent, whereby water diffuses into said core and therapeutic agent diffuses from said core into the environment of use at a particular time after exposure of said pellets to said environment of use;
   c) coating at least one additional population of cores uniformly with a coating as defined in claim 1, thereby forming at least one additional population of film coated pellets, said pellets having a defined permeability to water and said therapeutic agent, whereby water diffuses into said core and therapeutic agent diffuses from said core into the environment of use at a different particular time after exposure of said pellets to said environment than the particular times of other populations of pellets, each population of pellets having a mean release time separated by at least one hour from the mean release time of the other populations;
   d) mixing the different populations of pellets in a predetermined proportion mixture;
   e) forming aggregates of predetermined amounts of said mixture;
   f) holding each aggregate together within a capsule to prepare unit dosage forms.

18. A unit dosage form for administering a therapeutic agent into an aqueous fluid-containing environment in at least one pulsatile releasing event, said unit dosage form comprising:
   a) a capsule which does not maintain its integrity in the environment of use;
   b) at least one population of pellets held together by said capsule, said population of pellets arranged to release into said environment the therapeutic agent at a predetermined time after contact with said environment; and
   c) each pellet comprising: 1) a core including said therapeutic agent, and a modulating agent which is a different agent than the therapeutic agent, said modulating agent being soluble in water and providing an osmotic effect when dissolved; and 2) a release-controlling coating enclosing said core, said coating comprised of at least one water-permeable, film-forming, water-insoluble polymer material and hydrophobic agent, said hydrophobic agent a member selected from the group of hydrophobic agents consisting of fatty acids, wax and insoluble salts of fatty acids, said hydrophobic agent present in an amount of at least twenty-five percent of said water insoluble polymer material, all of said population of pellets being provided with a substantially uniform doating that causes water to enter said core and therapeutic agent to diffuse through the coating and into said environment at a time of at least one hour after exposure to said environment.

19. The unit dosage form according to claim 18, including a prompt-releasing supply of said therapeutic agent that is free of said release-controlling coating to thereby provide a two pulse dosage form in which a first pulse appears prompty after exposure to said environment of use from said prompt-releasing supply and a second pulse is delayed at least one hour by said release controlling coating.

20. The unit dose according to claim 19, in which said prompt-releasing supply of therapeutic agent is in pellet form.

* * * * *